United States Patent [19]

Scott et al.

[11] Patent Number: 5,332,732

[45] Date of Patent: Jul. 26, 1994

[54] THIOPHENE AND PYRIDINE ANTIPSYCHOTIC AGENTS

[75] Inventors: Malcolm K. Scott; Allen B. Reitz, both of Lansdale; Frank J. Villani, Jr., Perkasie; C. Royce Rasmussen, Lansdale, all of Pa.

[73] Assignee: McNeilab, Inc., Spring House, Pa.

[21] Appl. No.: 943,662

[22] Filed: Sep. 11, 1992

[51] Int. Cl.$^5$ ............... A61K 31/495; C07D 401/14
[52] U.S. Cl. ............... 514/212; 540/598; 544/58.4; 544/60; 544/357; 544/121; 544/364; 544/372
[58] Field of Search ............ 544/364, 372, 357, 121, 544/58.4, 60, 62; 540/598; 514/252, 227.8, 212, 235.8

[56] References Cited

U.S. PATENT DOCUMENTS 4,895,846  1/1990  Poindexter et al. ............ 514/252
5,144,035  9/1992  Mase et al. ............ 544/295

Primary Examiner—John M. Ford
Assistant Examiner—P. K. Sripada
Attorney, Agent, or Firm—Ralph R. Palo

[57] ABSTRACT

Compounds of the general formula I

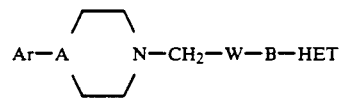

wherein A is N; Ar is aryl, substituted aryl or benzofuranyl, wherein the substituents are selected from $C_1$-$C_8$ alkoxy; B is CO or $CH_2$ and HET is selected from any of piperizine, piperidine, hexahydroazepine, morpholine, thiomorpholine or pyrrolidine, which may be substituted with one of more oxo groups are disclosed as novel antipsychotic agents. Pharmaceutical compositions and methods of treating convulsions employing such compounds of formula I are also disclosed.

22 Claims, No Drawings

THIOPHENE AND PYRIDINE ANTIPSYCHOTIC AGENTS

BACKGROUND OF THE INVENTION

Antipsychotic drugs are known to alleviate the symptoms of mental illnesses such as schizophrenia. Examples of such drugs include phenothiazine derivatives such as promazine, chlorpromazine, fluphenazine, thioridazine and promethazine, thioxanthenes such as chlorprothixene and butyrophenones such as haloperidol and clozapine. While these agents may be effective in treating schizophrenia, virtually all except clozapine produce extrapyramidal side effects, such as facial tics or tardive dyskinesia. Since antipsychotics may be administered for years or decades to a patient, such pronounced side effects may complicate recovery and further isolate the individual from society.

The present invention describes novel compounds that combine antipsychotic effects with minimal or reduced side effects such as extrapyramidal symptomology, and increased acid stability relative to some of the compounds known in the art.

SUMMARY OF THE INVENTION

Compounds of the general formula I

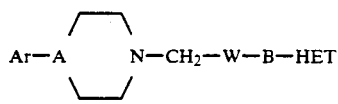

wherein Ar, A, B, W and HET are as defined hereinafter, are potent antipsychotic agents useful in the treatment of psychotic conditions such as schizophrenia in mammals including humans. The compounds of the present invention may also be useful in the treatment of other disorders of the central nervous system such as anxiety and aggression. The present invention is also directed to pharmaceutical compositions containing the compounds of formula I and methods of treating psychotic conditions employing such compounds.

DETAILED DESCRIPTION OF THE INVENTION

The present invention is directed to compounds of the general formula I:

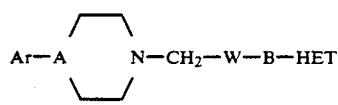

wherein

A is N or CH, but preferably N.

Ar is aryl or substituted aryl or heteroaryl. The aryl group may be independently substituted with one or more of $C_1$-$C_8$ alkyl, $C_3$-$C_{10}$ cycloalkyl, $C_1$-$C_8$ hydroxyalkyl, $C_1$-$C_8$ alkoxy, aryloxy, hydroxyl, trifluoromethyl, trifluoromethoxy, cyano, $C_1$-$C_8$ alkylthio, halogen, nitro, $C_1$-$C_8$ haloalkyl, amino or $C_1$-$C_8$ mono- or di-alkylamino. More preferably Ar is substituted phenyl or heteroaryl. When Ar is heteroaryl, the more preferred heteroaryl radical is benzofuranyl. The more preferred aryl substituents are selected from any of $C_1$-$C_8$ alkoxy. Most preferably, the substituent is isopropoxy. The preferred site of substitution is the 2-position on the phenyl ring.

W is a thiophene or pyridine ring. The thiophene ring is preferably attached to the $CH_2$ link (at the $CH_2$ that is connected to the piperidine or piperazine) at the 5 position on the thiophene ring and the pyridine ring is attached to the same $CH_2$ group at the 6 position on the ring.

B is CO or $CH_2$ forming a carbon chain link between the thienyl or pyridine ring and the HET ring, provided, however, that when W is pyridine B is $CH_2$.

HET is a 5-8 membered substituted or unsubstituted, saturated ring containing 1 or 2 hetero atoms selected from any of N, S or O, provided that at least one hetero atom is nitrogen selected from wherein the point of attachment of the ring to the remainder of the molecule is at a nitrogen. More preferably, the ring contains 6-7 members. Even more preferably, HET is selected from any of piperazine, piperidine, hexahydroazepine, morpholine, thiomorpholine, pyrrolidine, or heptamethyleneimine. Most preferably, HET is selected from either of piperidine or hexahydroazepine.

The HET ring may be independently substituted with one or more oxo substituents. The preferred substituent is a single oxo adjacent to the nitrogen which nitrogen is the point of ring attachment.

The HET ring is preferably attached to the thiophene ring via the carbon link at either the 2 or 3 position on the thiophene ring and attached to the pyridine ring via the carbon link at the 2 position on the pyridine ring. The HET ring is always attached to the carbon link via a ring nitrogen.

As used herein unless otherwise noted alkyl and alkoxy whether used alone or as part of a substituent group, include straight and branched chains. For example, alkyl radicals include methyl, ethyl, propyl, isopropyl, n-butyl, isobutyl, sec-butyl, t-butyl, n-pentyl, 2-pentyl, 2-methylbutyl, neopentyl, n-hexyl, 2-hexyl, 2-methylpentyl. Alkoxy radicals are oxygen ethers formed from the previously described straight or branched chain alkyl groups. Of course, if the alkyl or alkoxy substituent is branched there must be at least 3 carbons.

The term "aryl" as used herein alone or in combination with other terms indicates aromatic hydrocarbon groups such as phenyl or naphthyl. The term heteroaryl means aromatic hydrocarbon groups containing 1 or 2 hetero atoms selected from any of S, O or N. With reference to substituents, the term independently means that when more than one of such substituent is possible such substituents may be the same or different from each other.

Examples of particularly preferred compounds include:

1-[[5-[[1-[-(1-Methylethoxy)phenyl]-4-piperazinyl]methyl]-3-thienyl]carbonyl]piperidine;

Hexahydro-1-[[5-[[1-[2-(1-Methylethoxy)phenyl]-4-piperazinyl]methyl]-3-thienyl]carbonyl]-1H-azepine;

1-[[5-[[1-[2-(1-Methylethoxy)phenyl-4-piperazinyl]methyl]-2-thienyl]methyl]-2-piperidinone;

1-[[5-[[1-(7-Benzofuranyl)-4-piperazinyl]methyl]-2-thienyl]methyl]-2-piperidinone;

1-[[5-[[1-[2-(1-Methylethoxy)phenyl]-4-piperazinyl]methyl]-2-thienyl]carbonyl]piperidine;

Hexahydro-1-[[5-[[1-[2-(1-methylethoxy)phenyl]-4-piperazinyl]methyl]-2-thienyl]carbonyl]-1H-azepine; and 1-[[6-[[1-[2-(Methylethoxy)phenyl]-4-piperazinyl]methyl]pyridinyl]-methyl]-2-piperidinone.

Within the scope of the invention are compounds of the invention in the form of hydrates and other solvate forms.

Representative salts of the compounds of formula 1 which may be used include those made with acids such as hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluenesulfonic, cyclohexanesulfamic, salicyclic, p-aminosalicyclic, 2-phenoxybenzoic, 2-acetoxybenzoic or a salt made with saccharin. Such salts can be made by reacting the free base of formula I with the acid and recovering the salt.

The compounds of formula I may be prepared according to the following three reaction schemes.

REACTION SCHEME 1

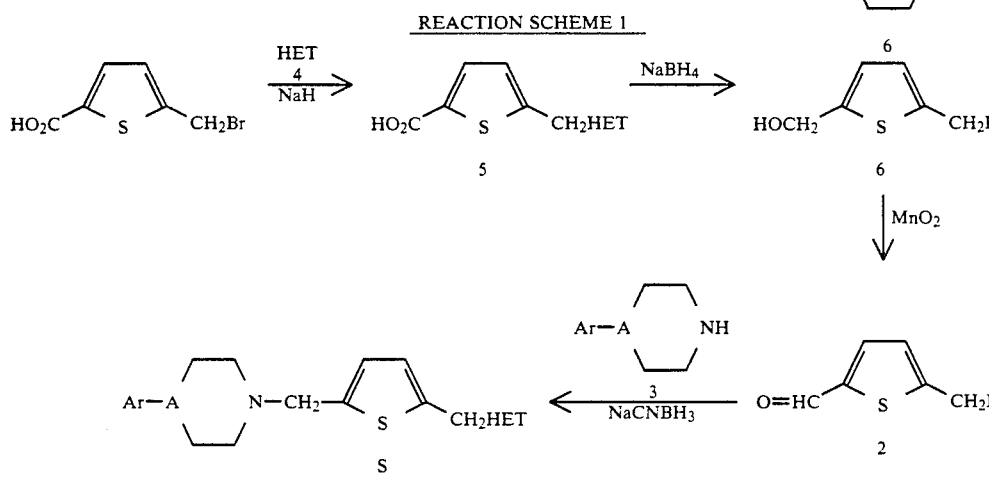

REACTION SCHEME 2

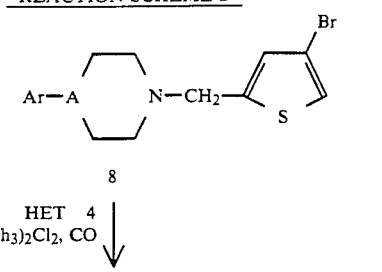

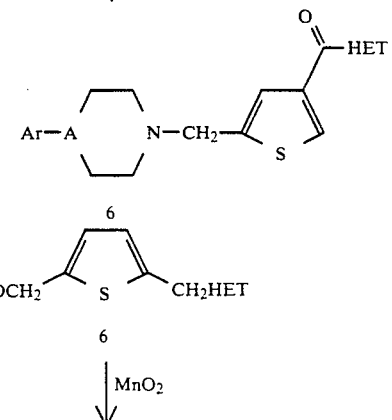

Reaction Scheme 1 displays the route to certain thiophene compounds of the invention (e.g. 1). Thiophene carboxaldehyde 2 is prepared by treating 5-bromomethyl-2-thiophenecarboxylic acid with a heterocylic moiety (4) such as a lactam in the presence of a suitable base (e.g. NaH) in a solvent such as toluene, followed by the reduction of the carboxylic acid 5 in ethanol or other suitable solvent using a reducing agent such as $NaBH_4$. Thereafter, the alcohol 6 is oxidized in methylene chlodde or other suitable solvent using a suitable oxidizing agent such as $MnO_2$ to produce the thiophene carboxaldehyde 2. Compound 2 is then reacted in methanol or other suitable solvent with an amine of formula 3 in the presence of a reducing agent such as $NaCNBH_3$ to produce the desired compound 1.

The 5-bromomethyl-2-thiophenecarboxylic acid, and the lactams as would be used for 4 are commercially available materials. Compounds 3 are either commercially available or may be made by known methods such as disclosed by Martin et. al. *J. Med. Chem.*, 1989, 32, 1052.

In Reaction Scheme 2, compounds of formula 6 are prepared by reacting a 4-bromothiophene of formula 8 with a heterocyclic amine of formula 4 (such as pyrrolidine or pyridine) in the presence carbon monoxide and a suitable catalyst such as bis(triphenylphosphine)palladium dichloride. Compounds of formula 8 are prepared from the reductive amination of 4-bromo-2-thiophenecarboxaldehyde with compounds of formula 3 in 1,2-dichloroethane or other suitable catalyst in the presence of glacial acetic acid using a reducing agent such as $NaBH(OAc)_3$.

REACTION SCHEME 2

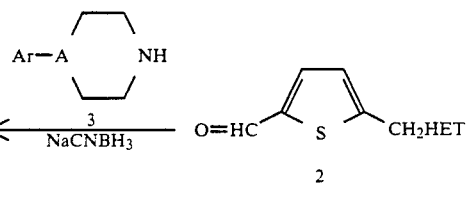

REACTION SCHEME 3

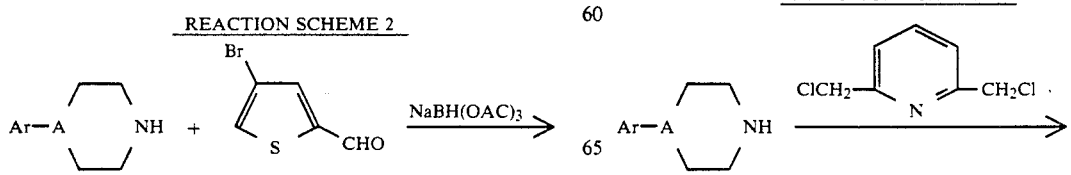

-continued
REACTION SCHEME 3

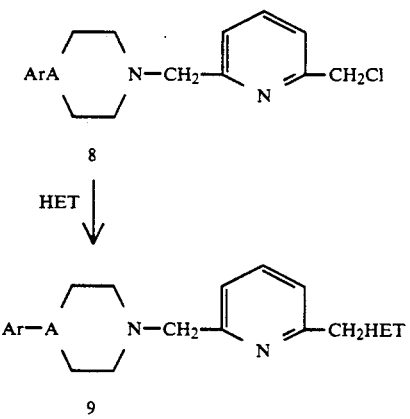

In Reaction Scheme 3, compounds of formula 9 are prepared by treating compounds of formula 8 with a metal salt, the metal being chosen from sodium, lithium, potassium and the like, of a suitable lactam (HET=lactam), using THF or another suitable solvent. Compounds of formula 8 are obtained from the reaction of 2,6-dichloromethylpyridine (Baker, et al, *J. Chem. Soc.*, 1958, 3594) and compounds of formula 3 in THF or other suitable solvent.

The antipsychotic activity of the compounds of the invention may be determined by the Block of Conditioned Avoidance Responding (Rat) test (CAR), the references being Cook, L. and E. Weidley in *Ann. N.Y. Acad. Sci.*, 1957, 6, 740–752, and Davidson, A. B. and E. Weidley in *Life Sci.*, 1976, 18, 1279–1284. Modulation of the dopamine-2(D-2) receptor is generally recognized to be beneficial in the treatment of schizophrenia (G. P. Reynolds *Trends Pharmacol. Sci.* 1992, 13, 116). Therefore, the affinity of the compounds of this invention were measured for the D-2 receptor. The CAR and D-2 binding tests were performed for compounds disclosed in this invention, and the data are listed in Table 1.

Block of Conditioned Avoidance Responding (Rat)

Apparatus: Rat operant chambers, housed within sound attenuated booths, both from Capden Instruments Ltd., were used in this test. The test chamber (8" H×90⅜" W×9" D) is constructed of aluminum and plexiglass with floor grid bars of stainless-steel (⅛" O.D.) spaced 9/16" apart. A stainless-steel operation level 1½" wide projects ¾" into the chamber and is positioned 2-2/8" above the grid floor. The shock stimulus is delivered via the grid floor by a Coulbourn Instruments solid state module. The parameters of the test and the collection of data are controlled automatically.

Training: Male, Fischer 344 rats obtained from Charles River (Kingston, N.Y.) weighing more than 200 g, are individually housed with chow and water provided ad libitum. The rats are trained for two weeks to approach criterion levels in the avoidance test (90% avoidance rate). One-hour training sessions are run at about the same time each day for four or five days a week. The training session consists of 120 tdals, with the conditioned stimuli presented every 30 sec. A trial begins with presentation of the conditioned stimuli (a light and a tone). If the rat responds by depressing the operant lever during the 15-second presentation of the conditioned stimuli, the trial is terminated and the animal is credited with a CAR. Failure to respond during the conditioned stimuli causes the presentation of the unconditioned stimulus (UCS), a 0.7 mA shock which is accompanied by a light and tone for five seconds. If the rat depressed the lever within the ten-second period, the shock and trial are terminated and an escape response recorded. If the rat fails to depress the lever during the UCS (shock), the trial is terminated after ten seconds of shock and the absence of a response is scored as a failure to escape. Intertrial level presses have no effect. If a rat performs at the 90% CAR level for two weeks, it is then run twice a week on the test schedule (see below) until baseline performance stabilized. Before any drug is administered, two weeks of CAR at a rate of 90% or better is required.

Determination of $ED_{50}$ Values

Trained rats are run in a one-hour session on two consecutive days at the same time and in the same test chamber each day. The sessions consist of 60 trials, one every minute. The conditioned stimuli are presented for 15 sec (maximum) and the unconditioned stimuli five sec (maximum). On Day 1, a vehicle solution is administered to the rats at a time preceding the trial run corresponding to the pretreatment time for the test compound. The route of administration and the volume of vehicle are also matched to that of the test compound. Only animals that exhibited greater than 90% CAR on Day 1 are given the test compound on Day 2.

Statistical Computations: ED50 values (that dose required to reduce the mean number of CARS to 50% of the control mean) are determined in the following manner. The percent change in CAR on the drug treatment day compared to vehicle pretreatment day is the key measure. The percent change (% change) in CAR is determined using the following formula:

$$\% \text{ change CAR} = ((\text{Day } 2\% \text{ CAR}/\text{Day } 1\% \text{ CAR}) \times 100) - 100$$

A negative number indicates a blockade of CAR, whereas a positive number would indicate increased CAR. The test results are reported as the mean % change for the group of rats. A reading of −20% is generally taken to represent a minimum value for a compound to be designated as active at a given dose in the CAR test. Failure to escape was calculated for each animal as follows:

$$\% \text{ Failures} = \# \text{ of Failures to Escape}/\# \text{ of trials}$$

The % failures, viz., loss of escape, is also reported as a group mean. Failures to escape are monitored closely and a session is terminated if ten failures occurred. $ED_{50}$ values and 95% confidence limits are calculated using linear regression analysis. The results of the CAR tests is shown in Tables 1.

Receptor Binding Assay

The dopamine $D_2$ binding activity of compounds was determined using a $P_2$ fraction (synaptosomal membranes) prepared from male, Wistar rats. The $D_2$ assay employed a $P_2$ fraction from the striatum, the ligand $^3$H-spiperone at a concentration of 0.05 nM, and 1 mM haloperidol as a blank determinant. Incubation was in 3 mM potassium phosphate buffer for 45 min at 37° C. Under these conditions, specific binding constituted 75% of total binding, and the $K_I$ values for some known drugs were: 0.37 nM for haloperidol and 82 nM for clozapine.

The data from this assay were analyzed by calculating the percent inhibition of the binding of the tritiated ligands by given concentrations of the test compound. $K_I$ values, where given, were obtained from the logit analysis of concentration-inhibition curves. A value of 1000 or less is generally taken to represent the value for a compound to be designated as active in this screen. If a compound is active in this screen, but not in the CAR screen, it is still considered an active antipsychotic agent because the CAR screen negative result may be due to site delivery problems which may be solved by a suitable delivery mechanism.

TABLE 1

| CP # | % Inhibition CAR, 5 mpk, PI | % escape loss | Receptor Binding ($K_I$ nM) D2 |
|---|---|---|---|
| 1 | −56 | 18 | 33 |
| 2 | −72 | 34 | 24 |
| 3 | −8 | 3 | 30 |
| 4 | −41 | 3 | 28 |
| 5 | −58 | 3 | 68 |
| 6 | −63 | 5 | 333 |
| 7 | −85 (15 mpk) | 0 | 2415 |

To prepare the pharmaceutical compositions of this invention, one or more compounds or salts thereof of the invention, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 50 to about 100 mg of the active ingredient, although other unit dosages may be employed.

In therapeutic use as an antipsychotic agent, the compounds of this invention may be administered in an amount of from about 0.5 to 5 mg/kg per day, and more preferably 1–3 mg/kg per day. The dosages, however may be varied depending upon the requirements of the patient, the severity of the condition being treated, and the compound being employed. Determination of optimum dosages for a particular situation is within the skill of the art.

The following examples describe the invention in greater detail and are intended to illustrate the invention, but not to limit it. In the Examples and Table 1, the CP #'s refer to the same compounds and not to the compounds in the reaction schemes. In the Examples, the terms $^1$H NMR, CI mass spec and IR indicate that the compounds produced were analyzed using such analyses and the results confirmed the structure.

EXAMPLE 1

1-[[5-[[1-[2-(1-Methylethoxy)phenyl]-4-piperazinyl]methyl]-2-thienyl]carbonyl]piperidine Fumarate (CP #1)

A mixture of 5-bromomethyl-2-thiophenecarboxylic acid (13.00 g, 0.059 mole) and $SOCl_2$ (20 mL) was refluxed for 1 hour. The excess $SOCl_2$ was evaporated and the residue was dissolved in $CH_2Cl_2$. After cooling in an ice bath, the solution was treated dropwise with a solution of piperidine (5.51 g, 0.065 mole), $NEt_3$ (6.50 g, 0.064 mole), and $CH_2Cl_2$ (25 mL) over 20 minutes. After stirring 15 minutes at 0° C., the reaction was poured onto ice and the organic layer was separated, washed with dilute HCl, 10% $Na_2CO_3$, and water. The organic layer was dried over $MgSO_4$, filtered and evaporated to a brown oil which was purified using HPLC (4:1/hexane/EtOAc eluant) affording a solid (8.10 g).

This material (2.88 g, 0.01 mole), N-[2-(methylethoxy)phenyl]piperazine fumarate (3.20 g, 0.095 mole), and N-methylpyrrolidinone (20 mL) were combined and stirred at room temperature for 4 hours. Then, $Na_2CO_3$ (2.10 g, 0.19 mole) was added and the mixture was stirred overnight at room temperature and then heated for 1 hour on a steam bath. The reaction mixture was poured into water and extracted with $Et_2O$. The organic layer was washed with water, brine solution, dried over $Na_2SO_4$, filtered, and evaporated to give 1-[[5-[[1-[2-(1-methylethoxy)phenyl]-4-piperazinyl]methyl]-2-thienyl]carbonyl]piperidine as an oil (3.36 g). This material was chromatographed on flash silica (98:2/$CHCl_3$:10% $NH_4OH$ eluant) to give an oil (2.10 g) which was treated with fumaric acid (0.57 g) in i-PrOH (40 mL). A crystalline solid formed which was collected and recrystallized from MeOH/i-PrOH producing 1-[[5-[[1-[2-(1-methylethoxy) phenyl]-4-piperazinyl]methyl]-2-thienyl]carbonyl]piperidine fumarate (2.08 g, 40%), m.p. 147.5°–148.5° C. $^1$H NMR and CI-MS support the structure.

Elemental Analysis: Calculated for $C_{24}H_{33}N_3O_2S \cdot C_4H_4O_4$: C, 61.86; H, 6.86; N, 7.72;. Found: C, 61.97; H, 6.92; N, 7.71.

EXAMPLE 2

1-[[5-[[1-[2-(1-Methylethoxy)phenyl]-4-piperazinyl]methyl]-3-thienyl]carbonyl]piperidine Monohydrochloride (CP #2)

A mixture of 1-[2-(methylethoxy)phenyl]piperazine (6.30 g, 0.029 mol), prepared as described by Martin and Scott, et al., *J. Med. Chem.*, 1989, 32, 1052–1056, 4-bromo-2-thiophenecarboxaldehyde (5.50 g, 0.029 mol), $NaBH(OAc)_3$ (8.00 g, 0.038 mol), acetic acid (1.70 g, 0.029 mol), and dichloroethane was stirred for several hours at room temperature. The reaction was then partitioned between diethyl ether/aqueous 10% $Na_2CO_3$ and the ether layer was separated, washed with saturated NaCl solution, dried over anhydrous $K_2CO_3$, filtered, and evaporated to give 1-[(4-bromo-2-thienyl) methyl]-4-[2-(1-methylethoxy)phenyl]piperazine (11.33 g) as a crude oil. Treatment of this material with HCl diethyl ether-isopropanol gave a crystalline solid which was recrystallized from methanol to give 1-[(4-bromo-2-thienyl)methyl]-4-[2-(1-methylethoxy) phenyl]piperazine monohydrochloride (10 g, 77%). A 2.0 g sample of this was recrystallized twice from methanol, and chromatographed on flash silica (99:1/$CHCl_3$:MeOH with 1% $NH_4OH$ as eluant). The resulting oil was converted to the hydrochloride salt, as described previously, and was recrystallized from methanol, and dried to give 1-[(4-bromo-2-thienyl) methyl]-4-[2-(1-methylethoxy) phenyl]piperazine monohydrochloride, m.p. (darkens 240° C.) 243°–249.5° C. $^1$H NMR and CI MS support the structure.

Elemental Analysis: Calculated for $C_{18}H_{23}BrN_2OS \cdot 1.5$ $HCl \cdot 0.5$ $H_2O$: C, 47.10; H, 5.60; N, 6.10; S, 6.98; Cl, 11.58: $H_2O$, 1.96. Found: C, 47.50; H, 5.38; N, 6.15; S, 6.97; Cl, 12.05; $H_2O$, 1.77.

A mixture of 1-[(4-bromo-2-thienyl) methyl]-4-[2-(1-methylethoxy) phenyl]piperazine (3.0 g, 0.0076 mole), piperidine (6.45 g, 0.0076 mole), and $Pd(PPh_3)_2Cl_2$ (100 mg) was placed in a bomb, purged with CO, and heated at 100° C. for 3 hours. An additional amount of piperidine (6.45 g, 0.0076 mole) was added and heating was continued overnight. The reaction mixture was purified using HPLC (gradient elution, 99:1/$CHCl_3$:10% $NH_4OH$ in methanol changing to 98:2) to give 1-[[5-[[1-[2-(1-methylethoxy)phenyl]-4-piperazinyl]methyl]-3-thienyl]carbonyl]piperidine as a clear syrup, 2.6 g. This material was converted to the monohydrochloride salt in isopropanol, using $Et_2O/HCl$. Recrystallization from isopropanol produced 1-[[5-[[1-[2-(1-methylethoxy)-phenyl]-4-piperazinyl]methyl]-3-thienyl]carbonyl]-piperidine monohydrochloride (1.82 g, 53%), m.p. 210.5°–212.5° C. $^1$H NMR and CI MS support the structure.

Elemental Analysis: Calculated for $C_{24}H_{33}N_3O_2S \cdot HCl$: C, 62.12; H, 7.38; N, 9.05. Found: C, 62.02; H, 7.31; N, 9.02

EXAMPLE 3

Hexahydro-1-[[5-[[1-[2-(1-methylethoxy)phenyl]-4-piperazinyl]methyl]2-thienyl]carbonyl]-1H-azepine Monohydrochloride Hemi Hydrate (CP #3)

The title compound was prepared by the method described in Example 2 to give 2.08 g(40%), m.p. 212°–215.5° C., except hexamethyleneimine was used in place of piperidine. $^1$H NMR and CI MS support the structure.

Elemental Analysis: Calculated for $C_{25}H_{35}N_3O_2S \cdot HCl \cdot 0.50H_2O$: C, 61.65; H, 7.66; N, 8.63; $H_2O$, 1.85. Found: C, 61.28; H, 7.80; N, 8.56; $H_2O$, 2.70.

EXAMPLE 4

Hexahydro-1-[5-[[-1-[2-(1-Methylethoxy)phenyl-4-piperazinyl]methyl]-3-thienyl]carbonyl]-1-H-azepine Hydrochloride Hydrate (CP #4)

Prepared as in Example 2, using hexahydroazepine in place of piperidine, was hexahydro-1-[[5 [[1-[2-(1-Methylethoxy)phenyl]-4-piperazinyl]methyl]-3-thienyl]carbonyl]-1-H-azepine monohydrochloride monohydrate (0.75 g, 25%), m.p. (darkens 195° C.) 199°–201° C. H-1 NMR and CI-MS support the structure.

Elemental Analysis: Calculated for $C_{25}H_{35}N_3O_2S \cdot HCl \cdot H_2O$: C, 60.53; H, 7.72; N, 8.47; $H_2O$, 3.63. Found: C, 60.87; H, 7.83; N, 8.61; $H_2O$, 3.35.

EXAMPLE 5

1-[[5-[[1-[2-(1-Methylethoxy)phenyl-4-piperazinyl]methyl]-2-thienyl]methyl]-2-piperidinone Hydrochloride (CP #5)

To a mixture of NaH (1.95 g,0.065 mol) in toluene (100 mL) was added 2-piperidinone (6.40 g, 0.065 mol) and the resulting mixture was stirred for 0.5 hour. After cooling in an ice bath, the mixture was treated dropwise with a solution of 5-bromomethyl-2-thiophenecarboxylic acid (11.8 g. 0.05 mol) and toluene (50 mL). The resulting blood-red mixture was stirred 1 hour, poured into ice water, and extracted with $Et_2O$. The ether layer was washed with dilute HCl, 10% $Na_2CO_3$, water, and brine. The ether layer was dried over $MgSO_4$, filtered, treated with charcoal, filtered, and evaporated to give a yellow semisolid, 5.6 g.

This material (4.40 g, 0.017 mol) and sodium borohydride (6.40 g, 0.017 mol) were combined in EtOH (100 mL) and refluxed for 8 hours. Water was added and the reaction was extracted $CHCl_3$. The organic layer was separated, dried over $MgSO_4$, filtered, and evaporated. The residue was chromatographed on flash silica (2:1/hexane:acetone eluant) to give 2.0 g of yellow oil. This material was dissolved in $CH_2Cl_2$, washed with 10% $Na_2CO_3$, separated, dried over $MgSO_4$, filtered, and evaporated to a yellow oil, 1.8 g.

The yellow oil material (1.70 g, 0.0075 mole) and $MnO_2$ (8.50 g , 0.097 mole) were combined in $CH_2Cl_2$ (70 mL) and stirred at room temperature for 1 hour. The reaction was filtered through diatomaceous earth and evaporated to give a yellow oil, 1.45g.

A solution of this oil (1.45 g, 0.0065 mole), N-[2-(methylethoxy)phenyl-piperazine (1.40 g, 0.0065 mole), glacial acetic acid (0.39 g, 0.0065 mole), and MeOH (20 mL) was treated with sodium cyanoborohydride (0.44 g, 0.007 mole) and the resulting mixture was stirred overnight at room temperature. The solvent was evaporated and the residue was slurried in 3N NaOH. Extraction with $Et_2O$, drying over $Na_2SO_4$, treatment with charcoal, and filtration and evaporation produced a clear oil. The material was chromatographed on flash silica(98:2/$CH_2Cl_2$:10% $NH_4OH$) to give 1-[[5-[[1-[2-(1-methylethoxy)phenyl]-4-piperazinyl]methyl]-2-thienyl]methyl]-2-piperidinone, 0.65 g. The HCl salt was prepared in $Et_2O$ and recrystallized from i-PrOH-/$Et_2O$ affording 1-[[5-[[1-[2-(1-methylethoxy)phenyl]-4-piperazinyl]methyl]-2-thienyl]methyl]-2-piperidinone monohydrochloride (0.64 g, 21%), m.p. 205°–209° C. $^1$H NMR and CI-MS support the structure.

Elemental Analysis: Calculated for $C_{24}H_{33}N_3O_2S \cdot HCl$: C, 62.12; H, 7.38; N, 9.05. Found: C, 61.84; H, 7.73; N, 8.74.

EXAMPLE 6

1-[[5-[[1-(7-Benzofuranyl)-4-piperazinyl]methyl]-2-thienyl]methyl]-2-piperidinone 1.5 Fumarate Hydrate (CP #6)

The title compound was prepared as described in Example 5, using 4-benzofuranylpiperazine in place of N-[2-(methylethoxy)phenyl]piperazine, m.p. 215°–220° C. The benzofuranyl piperazine was prepared as described in I. van Wijngaarden et al. (*J. Med. Chem.* 1988, 31, 1934). $^1$H NMR and CI-MS support the structure.

Elemental Analysis: Calculated for $C_{23}H_{27}N_3O_2S \cdot 1.5 \, C_4H_4O_4 \cdot H_2O$: C, 57.89; H, 5.86; N, 6.98. Found: C, 57.62; H, 6.19; N, 7.30.

EXAMPLE 7

1-[[6-[[1-[2-(Methylethoxy)phenyl]-4-piperazinyl]methyl]pyridinyl]methyl]-2-piperidinone Hydrochloride (CP #7)

A solution of 20 g of 2-(isopropoxy)phenylpiperazine fumarate in a minimal volume of water was treated with saturated aqueous NaHCO$_3$ until pH 8 was achieved, and then extracted twice with CH$_2$Cl$_2$. The combined organics were dried (MgSO$_4$), filtered, and concentrated to give 12.4 g (56.6 mmol) of the free base as an oil. This was then treated with 2,6-dichloromethylpyridine (29.8 g, 0.170 mol; Baker et al. *J. Chem. Soc.* 1958, 3594) and triethylamine 97.89 mL, 56.6 mmol). The brownish solution was heated at reflux in 200 mL of THF. After 3 hours, the solution was cooled, treated with 5.7 mL of concentrated HCl, ether, and ca. 50 mL of water. The product was extracted into the aqueous phase. It was then basified (saturated aqueous NaHCO$_3$), extracted into ether, and concentrated to give 19 g of 6-[[1-[2-(1-methylethoxy)phenyl]-4-piperazinyl]methyl]-2-chloromethylpyridine. The chemical-ionization MS was consistent with the assigned structure.

A solution of δ-valerolactam (3.86 g, 38.9 mmol) in 50 mL of THF was treated with nBuLi (15.57 mL of 2.5 M/hexane, 38.9 mmol) at 9° C. under nitrogen atmosphere. The resultant suspension was treated with 10 g (27.8 mmol) of 6-[[1-[2-(1-methylethoxy)phenyl]-4-piperazinyl]methyl]-2-chloromethylpyridine dissolved in 50 mL of DMF. The solution was heated at reflux, whereupon the lactam anion went entirely into solution. After 2 hours, the solution was cooled and treated with water and the product was extracted twice into ether. The combined ether layers were dried (MgSO$_4$), filtered, and concentrated. The resultant oil was washed with water and then purified on two Waters Prep 500 columns, first with CHCl$_3$/MeOH/NH$_4$OH (96:3.5:0.5), and then with CH$_2$Cl$_2$/MeOH/NH$_4$OH (94.3:5.0:0.7). A pure fraction of 5.84 g of material was obtained. This was dissolved in iPrOH and filtered through a Millipore filter and treated with 2.72 mL of concentrated HCl. Trituration with ether caused a voluminous precipitate to emerge, which was recrystallized from iPrOH/ether. This solid was dried at 65° C. overnight under vacuum to give 3.3 g (23%) of 1-[[6-[[1-[2-(methylethoxy)phenyl]-4-piperazinyl]methyl]-pyridinyl]methyl]-2-piperidinone hydrochloride, m.p. 180°–183° C. The $^1$H NMR and CI-MS were consistent with the assigned structure.

Elemental Analysis: Calculated for $C_{25}H_{34}N_4O_2 \cdot 2.6HCl$: C, 58.04; H, 7.13; N, 10.83; Cl, 17.82. Found: C, 57.75; H, 7.25; N, 10.64; Cl, 17.90.

We claim:

1. A compound of the formula I:

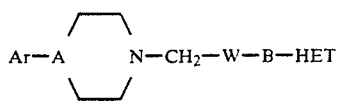

wherein
A is N
Ar is aryl substituted aryl or benzofuranyl, wherein the aryl substituents are seleted from C$_1$–C$_8$ alkoxy;
B is CO or CH$_2$;
W is thiophene or pyridine;
HET is selected from any of piperizine, piperidine, hexahydroazepine, morpholine, thiomorpholine or pyrrolidine, which may be substituted with one or more oxo groups, or the pharmaceutically acceptable salt thereof.

2. The compound of claim 1, wherein B is CO.
3. The compound of claim 1, wherein W is thiophene.
4. The compound of claim 1, wherein W is pyridine.
5. The compound of claim 1, wherein the HET ring substituent is a single oxo group.
6. The compound of claim 1, wherein the HET ring is a substituted or unsubstituted piperidine or hexahydroazepine ring.
7. The compound of claim 6, wherein B is CO.
8. The compound of claim 5, wherein the HET ring is piperidine and the substituent is a single oxo group.
9. The compound of claim 1, wherein Ar is substituted aryl or benzofuranyl.
10. The compound of claim 9, wherein Ar is substituted with C$_1$–C$_8$ alkoxy.
11. The compound of claim 10, wherein the substituent is isopropoxy.
12. The compound of claim 1 having the name 1-[[5-[[1-[2-(1-methylethoxy)phenyl]-4-piperazinyl]methyl]-3-thienyl]carbonyl]piperidine.
13. The compound of claim 1, having the name hexahydro-1-[[5-[[1-[2-(1-methylethoxy)phenyl]-4-piperazinyl]methyl]-3-thienyl]carbonyl]-1H-azepine.
14. The compound of claim 1, having the name 1-[[5-[[1(7-benzofuranyl)-4-piperazinyl]-2-thienyl]-2-piperidinone.
15. The compound of claim 1, having the name 1-[[5-[[1-[2-(1-methlethoxy)phenyl]-4-piperazinyl]methyl]-2-thienyl]carbonyl]piperidine.
16. The compound of claim 1 having the name hexahydro-1-[[5-[[1-[2-(1-methylethoxy)phenyl]-4-piperazinyl]methyl]-2-thienyl]carbonyl]-1H-azepine.
17. The compound of claim 1 having the name 1-[[6-[[1-[2-(methylethoxy)phenyl]-4-piperazinyl]methyl]-pyridinyl]methyl]-2-piperidinone.
18. The compound of claim 1 having the name 1-[[5-[[1-[2-(1-methylethoxy)phenyl]-4-piperazinyl]methyl]-2-thienyl]methyl]-2-piperidinone.
19. A composition for treating psychotic conditions in mammals comprising the compound of claim 1 and a pharmaceutically acceptable carrier, said compound being present in a therapeutically effective amount for treating psychotic conditions in mammals.
20. A method for treating psychotic conditions in mammals comprising administering to a mammal in need of such treatment the compound of claim 1 in an amount sufficient to treat such conditions.
21. The method of claim 20, wherein the condition is schizophrenia.
22. The method of claim 20, wherein the effective amount is about 0.5 to 5 mg/kg per day.

* * * * *

UNITED STATES PATENT AND TRADEMARK OFFICE
CERTIFICATE OF CORRECTION

PATENT NO. : 5,332,732
DATED : July 26, 1994
INVENTOR(S) : Malcolm K. Scott, et al.

It is certified that error appears in the above-indentified patent and that said Letters Patent is hereby corrected as shown below: On title page,

In the Abstract, line 6, change "piperizine" to --piperazine--.

In Col. 12, line 10, insert a comma after the word "aryl".

In Col. 12, line 42, after "-4-piperazinyl]", insert the word --methyl--.

In Col. 12, line 42, after "-2-thienyl]", insert the word --methyl--.

Signed and Sealed this

Twenty-fifth Day of April, 1995

Attest:

BRUCE LEHMAN

*Attesting Officer*     *Commissioner of Patents and Trademarks*